United States Patent [19]

Innocenti

[11] Patent Number: 5,011,663
[45] Date of Patent: Apr. 30, 1991

[54] MULTITEST-TUBE FOR CLINICAL CHEMISTRY ANALYSIS FOR SEVERAL SIMULTANEOUS TESTS

[75] Inventor: Alberto Innocenti, Florence, Italy
[73] Assignee: S E A C s.r.l., Florence, Italy
[21] Appl. No.: 567,688
[22] Filed: Aug. 13, 1990

Related U.S. Application Data

[63] Continuation of Ser. No. 76,541, Jul. 22, 1987, abandoned.

[51] Int. Cl.$^5$ ............................................. B01L 3/00
[52] U.S. Cl. ........................................ 422/102; 422/72; 436/177; 436/809; 435/301; 435/808; 356/244; 356/246
[58] Field of Search .................. 422/102, 72; 436/177, 436/809; 435/301, 808; 356/244, 246

[56] References Cited

U.S. PATENT DOCUMENTS

| | | | |
|---|---|---|---|
| 3,071,316 | 1/1963 | Piemonte et al. | 422/72 X |
| 3,415,627 | 12/1968 | Rait | 422/72 |
| 3,681,029 | 8/1972 | Shapiro | 422/72 X |
| 3,976,579 | 8/1976 | Bennett | 422/72 X |
| 4,239,853 | 12/1980 | Bradley | 422/72 X |
| 4,373,812 | 2/1983 | Stein et al. | 422/72 X |
| 4,462,964 | 7/1984 | Guigan | 422/72 X |
| 4,566,790 | 1/1986 | Mandle | 422/102 X |
| 4,689,203 | 8/1987 | Kaartinen et al. | 422/102 X |
| 4,708,850 | 11/1987 | Husain | 422/102 X |

*Primary Examiner*—David L. Lacey
*Assistant Examiner*—Lynn M. Kummert
*Attorney, Agent, or Firm*—McGlew & Tuttle

[57] ABSTRACT

A test-tube for clinical chemistry analysis made up of a plurality of cells, each one of the cells comprising a lower portion for the collection of the reagent and a side intermediate portion provided with an edge for the storage of the sample to be tested upon the mixing thereof with the reagent. The cells are disposed in a straight configuration. The operations of the mixing of the samples with the reagents and the simultaneous stirring inside all cells, may be carried out by imparting the test-tube with an angular motion about a longitudinal axis.

3 Claims, 1 Drawing Sheet

U.S. Patent — Apr. 30, 1991 — 5,011,663
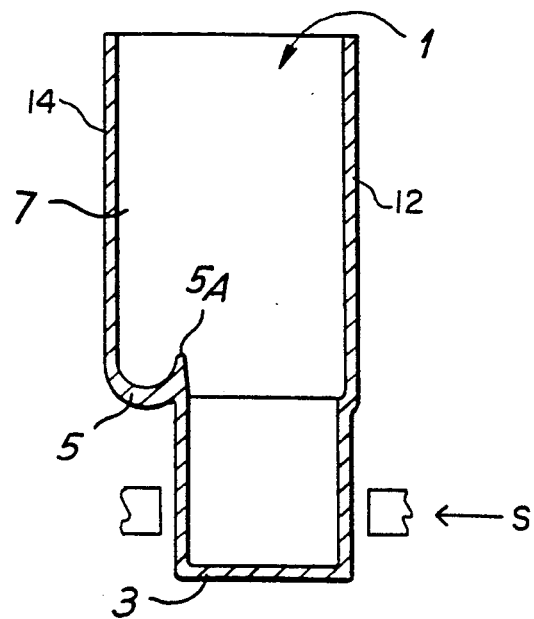
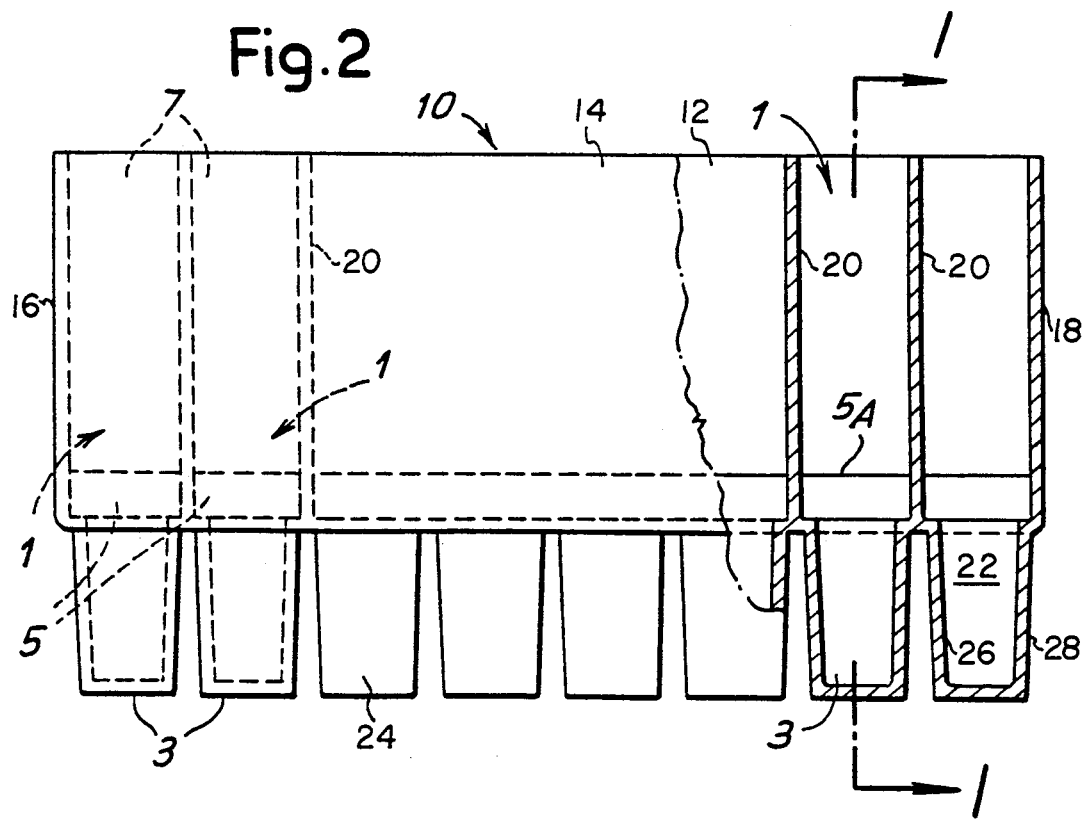

MULTITEST-TUBE FOR CLINICAL CHEMISTRY ANALYSIS FOR SEVERAL SIMULTANEOUS TESTS

This is a file wrapper continuation application of application Ser. No. 076,541 filed Jul. 22, 1987, now abandoned.

FIELD AND BACKGROUND OF THE INVENTION

In the clinical chemistry analysis of, for example, cholesterol, triglycerides, glycemia, transaminase, it is important that readouts can be carried out on different samples treated as homogeneously as possible especially as far as the times of mixing the sample with the reagents and the temperatures of the sample under test and those of the reagent are concerned. It is also desirable to carry out surveys, that is, detections like photometric readouts in very short and closely spaced time intervals, to ensure in particular the homogeneity of the data taken from a number of sequentially tested samples.

SUMMARY AND OBJECT OF THE INVENTION

It is an object of the invention to provide a test-tube, for the above-mentioned analysis, which accomplishes the above mentioned purposes and, in particular, being made up of a plurality of cells, each one comprising a lower portion for the collection of the reagent and a side intermediate portion defined by an edge, for the storage or the containing of the sample to be tested. These cells are preferably located side-by-side in a straight configuration. With the arrangement according to the invention is possible to carry out—through oscillations of the multitest-tube—the operations for the mixing of the sample with the reagent as well as the simultaneous stirring inside all the cells which form the test-tube, thereby ensuring the uniformity of each stir and, in practice, also the uniformity of the temperature of the treated samples and reagents.

Moreover, the straight configuration of the test tube allows a rapid and sequential reading for all the samples of the set of cells, through the sliding of a sensor with respect to the multitest-tube, or viceversa. The homogeneity of surveys which results is therefore ensured for all the tests which result almost simultaneously although performed by means of a single sensor.

For optical tests it is of advantage to make the lower portions of the cells of a prismatic shape with walls of uniform thickness, the walls being optically transparent.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which a preferred embodiment of the invention is illustrated.

BRIEF DESCRIPTION OF THE DRAWINGS

In the Drawings:

FIG. 1 shows a longitudinal section of a cell taken on line I—I of FIG. 2;

FIG. 2 shows a front view of a multitest-tube according to the model.

DESCRIPTION OF THE PREFERRED EMBODIMENT

Referring to the drawing in particular, numeral 1 generally indicates a cell forming the unit element of the multitest-tube, generally indicated by 10. The cell 1 has a lower portion 3 of prismatic shape and uniform thickness, wherein a reagent is introduced, a second side portion 5 with an edge 5A, wherein the sample to be tested is introduced, and a third upper portion 7; the portions 7 of the cells, joined between them, make up the body of the multitest-tube and have the function of holding the reagent during the mixing.

Inside the portions 5 and 3 of the multitest tube 10 thus, several samples to be tested and several reagents, may be respectively introduced without any particular difficulty for the operator. In particular, it is possible to carry out, by a single multitest tube 10, different tests on the same sample, the same test on different samples or different tests on different samples. In any case, once the multitest-tube 10 has been properly loaded with samples and reagents, it can be put into oscillation, about a horizontal longitudinal axis, with suitable amplitude and frequency of oscillation until causing the overflow of the reagent from zone 5 to zone 3 and the consequent mixing between reagent and sample. It is also possible to simultaneously stir the various mixtures formed as above mentioned, by moving the test-tube along an annular trajectory in a horizontal plane, to perform both the mixing and the homogenization.

With the described operation, it is possible to provide uniformity in the moment of the sample/reagent mixing and the time for the stirring of all the samples under test. It is also possible, owing to the test-tube configuration, to operate under conditions of uniform temperatures of different samples and reagents, by waiting to provide for the necessary incubation time, for the time being carried out, before the mixing.

Once the mixing and the stirring are completed, and the decantation time possible prescribed for the test being carried out is elapsed, the readouts on the samples held in the several cells 1 can be sequentially made by sliding a sensor S, facing the straight front surface formed by portions 3 of the cells 1 making up the multitest-tube 10, or viceversa.

Through this disposition a fast readout of data relevant to each cell can be made thus ensuring uniform results.

This type of test-tube allows the fulfillment of the requirements for clinical chemistry tests that may be kinetic, colorimetric and of other type.

While a specific embodiment of the invention has been shown and described in detail to illustrate the application of the principles of the invention, it will be understood that the invention may be embodied otherwise without departing from such principles.

I claim:

1. A multi test-tube construction for clinical test tube analysis comprising: a planar front wall; a planar rear wall substantially parallel to said front wall; first and second planar side walls, substantially perpendicular to said front and rear walls, each side wall being connected to said front and rear walls; a plurality of intermediate side wall members, substantially parallel to said side walls, positioned between and connected to said front and rear walls forming a plurality of cells with said front and rear walls, the outermost of said plurality of intermediate side wall members forming outermost cells with said first and second planar side walls and said front and rear walls; a plurality of lower portions, each lower portion being associated with each cell, each said lower portion having a bottom wall, a lower portion planar front wall connected to said front wall, a lower portion planar rear wall, a first lower portion planar side wall and a second lower portion planar side wall, said lower portion planar side walls being each connected to one of said first side wall, second side wall or intermediate side wall; a plurality of side portions associated with each cell, each side portion being connected to said rear wall and said lower portion rear wall, each of said side portions forming a cavity region between said rear wall and corresponding said lower rear wall portion with an edge separating each of said side portions from said lower portion in a horizontal direction for storage of a sample to be tested, each of said walls being transparent so as to allow optical sensing and visual inspection, reagents positioned in respective cavities of said side portions overflowing into said lower portion, holding a sample or the like, upon oscillation about a horizontal longitudinal axis, of the multi test-tube construction, of suitable amplitude and frequency allowing investigation of a plurality of samples or reagents in the corresponding plurality of cells under uniform conditions.

2. A multi test-tube construction according to claim 1, wherein: the walls of each of said lower portions are of a uniform thickness to provide better optical transparency.

3. A multi test-tube construction according to claim 1, further comprising a sensor which may be positioned adjacent one of said lower portions of said plurality of lower portions for movement relative thereto and for sliding along each of said lower portions.

* * * * *